US008255241B2

(12) United States Patent
Cafer

(10) Patent No.: US 8,255,241 B2
(45) Date of Patent: Aug. 28, 2012

(54) ICONIC GRAPHICAL METHOD FOR DISPLAYING COMPLEX INFORMATION

(76) Inventor: Jason Edward Cafer, Columbia, MO (US)

( * ) Notice: Subject to any disclaimer, the term of this patent is extended or adjusted under 35 U.S.C. 154(b) by 917 days.

(21) Appl. No.: 11/866,986

(22) Filed: Oct. 3, 2007

(65) Prior Publication Data

US 2010/0017754 A1 Jan. 21, 2010

Related U.S. Application Data

(63) Continuation-in-part of application No. 11/695,050, filed on Apr. 1, 2007.

(51) Int. Cl.
*G06Q 10/00* (2012.01)
(52) U.S. Cl. ............................... 705/3; 705/2
(58) Field of Classification Search .................. 705/2, 3
See application file for complete search history.

(56) References Cited

U.S. PATENT DOCUMENTS

| 5,995,938 | A  | * | 11/1999 | Whaley ........................... 705/3 |
| 6,710,713 | B1 | * | 3/2004  | Russo ......................... 340/573.1 |
| 2002/0042723 | A1 | * | 4/2002 | Rice et al. ......................... 705/2 |
| 2005/0091609 | A1 | * | 4/2005 | Matthews et al. ............. 715/804 |
| 2006/0080140 | A1 | * | 4/2006 | Buttner et al. ................... 705/2 |
| 2007/0250346 | A1 | * | 10/2007 | Luciano et al. ................. 705/2 |

* cited by examiner

*Primary Examiner* — Vivek Koppikar
*Assistant Examiner* — Edward Winston, III
(74) *Attorney, Agent, or Firm* — R. Scott Kimsey

(57) ABSTRACT

The present invention is directed to a method of providing information regarding a patient's use of medications, the method including the step of providing a graphical icon relating to the medication, the graphical icon including at least one indicator relating to the patient's use of the medication. The least one indicator preferably provides information such as dosage information, duration information, compliance information, and impression information.

11 Claims, 13 Drawing Sheets

ICONIC GRAPHICAL METHOD FOR DISPLAYING COMPLEX INFORMATION

CROSS-REFERENCE TO RELATED APPLICATIONS

This application is a Continuation-In-Part of U.S. patent application Ser. No. 11/695,050, filed on Apr. 1, 2007, which is incorporated herein by reference in its entirety.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

BACKGROUND OF THE INVENTION

This invention relates generally to a graphical method for displaying complex information to an individual, and more specifically to a method of displaying such information using at least one graphical icon, whereon information is represented in an easy to understand and assimilate manner. The present invention has particular utility in the medical field, with respect to displaying medication information and the medication history of a patient to a physician or other individual. The present invention is, however, adaptable for use in any industry in which complex information is displayed to an individual, particularly when that information spans a period of time.

In many industries or other areas of human endeavor, complex information must be assessed and understood by an individual in as efficient a manner as possible. Unfortunately, such information is often provided in the form of multiple pages of written material, each perhaps being located in a separate physical area, making retrieval and review of the information tedious and time-consuming.

The advent of modern computer systems has eliminated or attenuated some of the problems associated with information review. Information once present at various physical locations can now be summoned electronically, appearing on a user's computer screen regardless of where the actual file is stored. The user of local-area networks and the internet have been particularly important in terms of the rapid retrieval of complex or large amounts of information. Even so, problems remain, as described below.

In the case of the medical professions, for example, where complex historical information must often be readily available to a practitioner, and readily assimilated thereby, it is estimated the approximately fifteen percent of the time spent with respect to a given patient is spent retrieving data concerning that individual from the medical record. Such information includes data on the medications being taken by a patient, as well as the medication history of that patient.

As the sophistication of electronic technologies has increased, such technologies have been used to address inefficiencies in accessing and assimilating medical information. Difficulties have remained, however, in part due to the failure to adapt traditional thinking to the modern electronic environment. Many electronic medical information systems have essentially ported the traditional medical record and accompanying information to an electronic environment, with little or no adaptation of the information to take advantage of this new environment. This had led to some increase in efficiency in terms of accessing medical information. Many of the other inefficiencies of traditional medical information systems, however, remain unaddressed. In some cases, existing electronic medical information systems may even be less effective than traditional paper charting.

In addition to the above, numerous other inefficiencies exist in the current physician/patient information regimen, whether mediated primarily by electronic or paper forms of record keeping. What is needed, in the medical field, is a method that takes full advantage of the graphical power of an electronic interface for swift access to, comprehension of, and utilization of medical information. What is needed in other industries and endeavors is, similarly, a method of providing information to a person in a manner that is swift, easy to assimilate, and takes full advantage of an electronic graphical interface.

BRIEF SUMMARY OF THE INVENTION

The present invention is directed to a method of providing information regarding a patient's use of medications, the method including the step of providing a graphical icon relating to the medication, the graphical icon including at least one indicator relating to the patient's use of the medication.

In another aspect of the present invention, the at least one indicator provides historical information concerning the patient's use of the medication.

In another aspect of the present invention, the at least one indicator provides information such as dosage information, duration information, compliance information, and impression information.

In another aspect of the present invention, the at least one indicator is a dosage indicator, duration indicator, impression indicator, or compliance indicator.

In another aspect of the present invention, the graphical icon provided includes an image of the medication being taken by the patient.

In still another aspect of the present method, the step of providing the graphical icon is repeated for each medication being taken by a patient, thereby providing a set of graphical icons representing all of the medications being taken by a patient.

The present invention further provides a graphical icon for providing medical information relating to a patient, the graphical icon including a dosage indicator, duration indicator, compliance indicator, and impression indicator.

In still another aspect of the present invention, a graphical icon is provided, the graphical icon including an enclosed geometric shape having a plurality of edges and at least one indicator for providing information related to a subject matter of the graphical icon. At least one of the plurality of edges is an axis of the at least one indicator.

In another aspect of the present invention, the subject matter of the graphical icon is medical, legal, automotive, financial, or computer files, folders, and applications subject matter.

In another aspect of the present invention, the graphical icon includes a text portion for conveying textual information to the user of the graphical icon.

In another aspect of the present invention, the graphical icon is associated with an electronic database and at least a portion of the information conveyed by the graphical icon reflects information contained within the database.

DETAILED DESCRIPTION OF THE INVENTION

Figure 1:
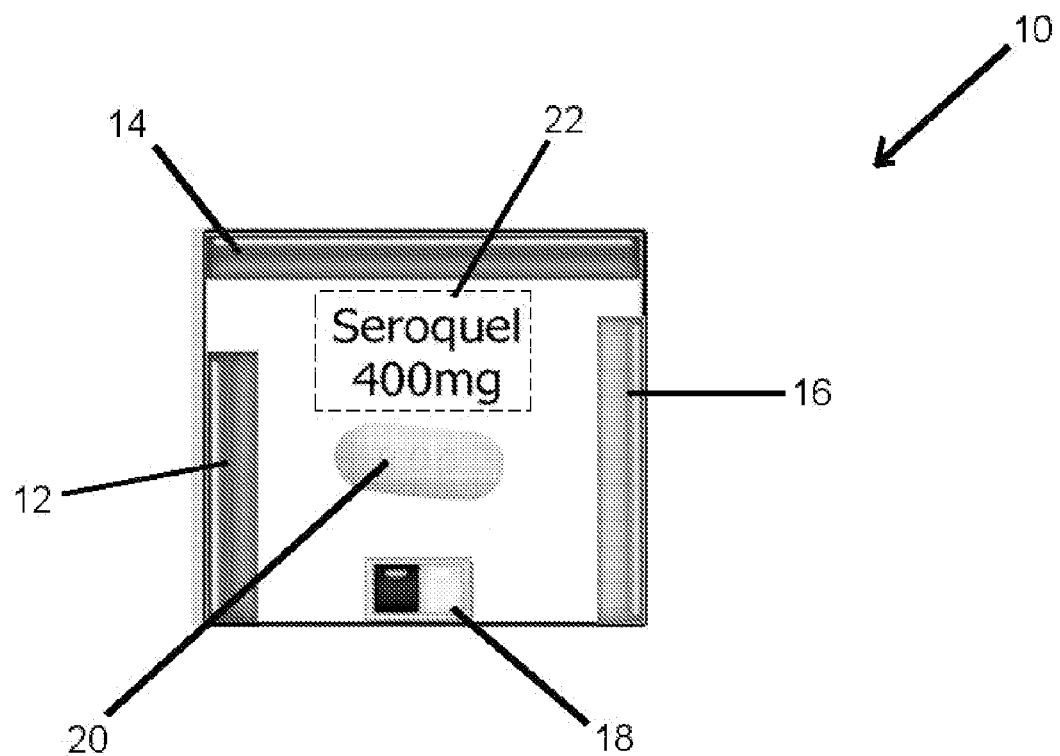
FIG. 1 is an exemplary depiction of a medication icon embodiment of a graphical icon according to the present invention.

Various terms are used below in interchangeable or broad fashion. For example, the term 'indicator,' as used herein, may be used to describe any indicia, indicator, symbol, text, or other representation contained on a graphical icon of the present invention for the purpose of imparting information. Thus, the various bars, such as dosage and impression bars, as well as adjustment, warning, augmentation, and year indicators, medication or other images, and the like described below may all be referred to generally as 'indicators.' Also, the term 'graphical icon' is used herein broadly to refer to any graphical representation according to the present invention, including the exemplary medication icon embodiments of the present invention described in detail below, or any other embodiments of the present invention whether or not expressly described herein.

Before turning to a detailed description of each of the present invention, basic hardware and software information is now provided. The present invention may be implemented on any suitable computer, which may include but is not limited to a desktop personal computer, a laptop or notebook computer, a server-type computer system, or a personal digital assistant. Any suitable computer system may be used to run software developed in accordance with the present invention. Likewise, any suitable computer operating system may be used to run software developed in accordance with the teachings of the present invention. Such operating systems include, but are not limited to, any of the various versions of Microsoft Windows, MacOS, Linux distributions, and OS/2. Finally, it will be apparent to those of skill in the art upon reading this disclosure that the teachings of the present invention can be implemented using any of a variety of computer programming languages. It is contemplated that any suitable language may be used and that the use of one rather than another does not depart from the spirit or scope of the present invention. Examples of programming languages that may be used include, but are not limited to, Java, C, C++, BASIC, Visual Basic, Python, COBOL, ASP, Perl, .NET, PHP, and combinations thereof.

The present invention may be implemented via a web-based software application, a stand-alone software application, or a combination of both. The various features of the present invention that require a degree of networking may utilize an established wide-area network, such as the internet, or may run entirely on a local-area network (LAN) or via dedicated network lines that, while not local, are directed exclusively toward implementation of the present invention. Any suitable network type may be used in conjunction with the present invention.

Any typical functionality associated with software programs, whether web-based or otherwise, may be incorporated into the present invention without departing from the scope of the invention. This includes but is not limited to such features as drop-down menus, checkboxes, the ability to resize and reposition windows, the ability to lock window sizes and positions, and the like.

In addition to the above, it is further contemplated that the present invention may be provided in hard copy form, such as printed on paper or other material. Although such information would not be dynamic in the same sense as the electronic information described above, the ability to convey complex information is retained.

Turning now to the drawings, wherein like numerals represent like parts, the numeral 10 refers generally to a graphical icon constructed in accordance with the teachings of the present invention. As shown in FIG. 1, graphical icon 10 is a medication icon or "medication iconograph" used for conveying medication information to an individual. This is an exemplary embodiment of graphical icon 10 of the present invention, and will be the primary exemplary embodiment of the present invention described in this paper. Other embodiments of a graphical icon according to the present invention will be described further below, including a generalized description of the principles of the present invention absent any particular type of information to be conveyed. Graphical icon 10 shown in FIG. 1 preferably includes a dosage bar 12, duration bar 14, compliance bar 16, impression bar 18, medication image 20, and text box 22.

In the embodiment of graphical icon 10 shown in FIG. 1, dosage bar 12 is a visual representation of the dosage of a medication represented by graphical icon 10 being received by a given patient. At a glance, a user can tell whether a given patient is receiving a high dosage, a low dosage, or some intermediate dosage. A greater height of dosage bar 12 indicates a greater dosage of the indicated medication being taken by the patient. Further, dosage bar 12 preferably further includes, as needed, at least one arrow or other directional image indicating whether a given patient is receiving an increased dosage of the medication represented by graphical icon 10, or whether the patient is receiving a decreased dosage, due to some interaction with, for example, another medication being taken by the patient. Such images or other indicia indicating increased or decreased dosages may be termed 'adjustment indicators,' or 'augmentation indicators' as described below. In situations wherein a graphical icon 10 of the present invention, such as a medication icon shown in FIG. 1, is associated with an automated or electronic medical record or management system, the system is preferably able to accesses a medical reference or other database in order to obtain a usual dosage, and dosage bar 12 initially represents this usual dosage. Changes made to the reference database will preferably be reflected in the files pertaining to all patients who are taking the medication or medications for which information in the medical reference database has been altered.

Figure 2:
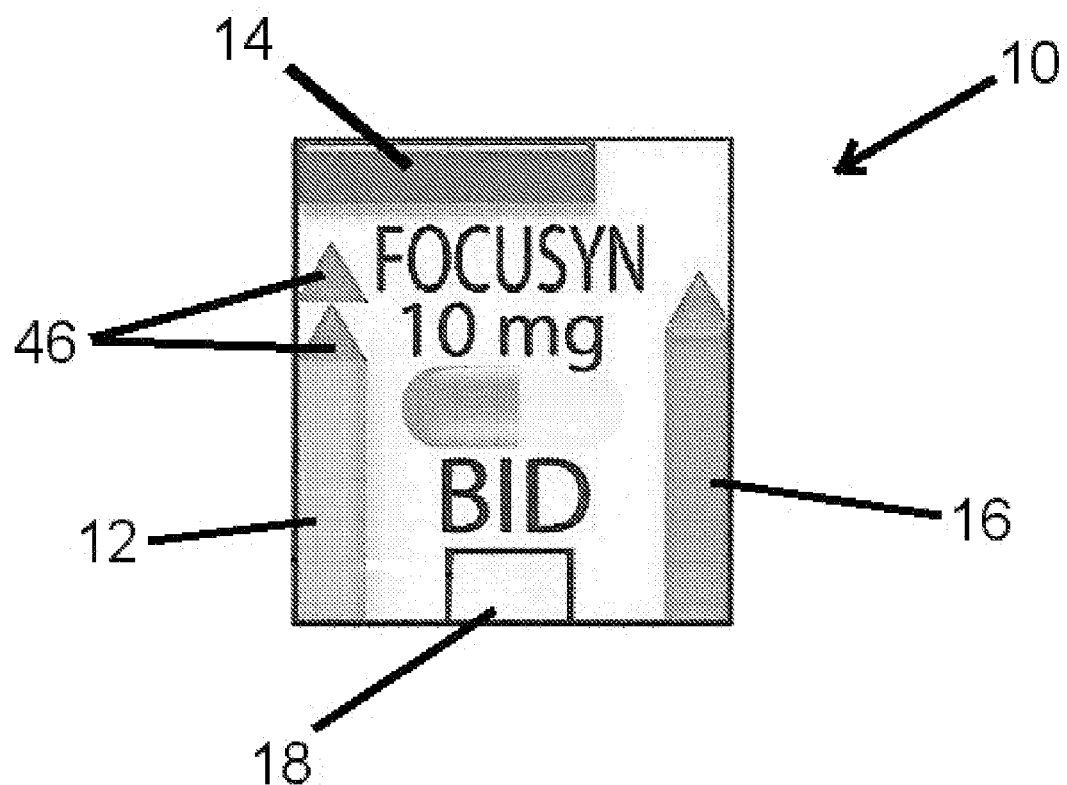
FIG. 2 is an exemplary embodiment of a graphical icon of the present invention having adjustment indicators associated therewith.

In such situations wherein graphical icon 10 is associated with an electronic medical records system, or other electronic system for managing patients, medical care, and the like, a user of the electronic system may be able to change the dosage by clicking on dosage bar 12 with a mouse or other pointer and assigning a new dosage to the patient. Dosage bar 12 preferably incorporates additional features into the representation displayed to a user when the dosage is being modified based upon, for example, interactions with other medications, as best shown in FIG. 2. The change in dosage due to drug interactions may be represented, for example, from +2 to −2, with two triangles 46 (adjustment indicators) pointing upward indicating a +2 degree upward adjustment in dosage. Two triangles 46 pointing in a downward direction may be utilized to indicated a −2 degree downward adjustment in dosage. Triangles 46 are preferably located at or near the top of dosage bar 12 or, in some cases, overlapping at least a portion of dosage bar 12. The interaction information is preferably initially based upon data in a medical reference database associated with the electronic system being utilized and having graphical icons 10 associated therewith. For example, a medical reference database may indicate that valproate's effect on lamotrigine levels is +2, while lamotrigine's effect on valproate levels is 0. Based on a default medical reference database, the +2 effect of lamotrigine on valproate levels will be indicated by two triangles 46 pointing upward from dosage bar 12 of the valproate graphical icon.

Figure 3:
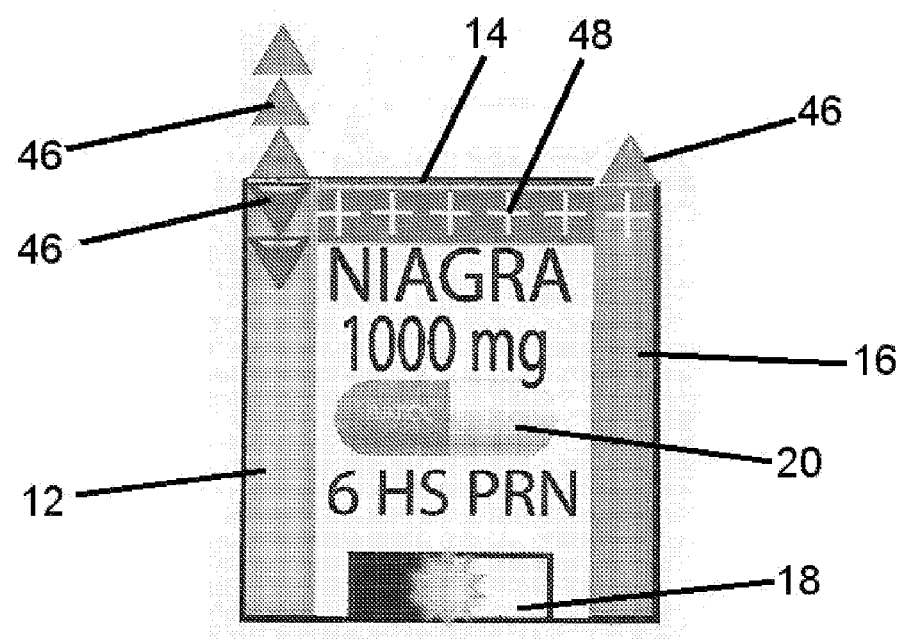
FIG. 3 is an exemplary embodiment of a graphical icon of the present invention having adjustment indicators, year indicators, and warning indicators associated therewith.

FIG. 3 provides an illustration of a graphical icon 10 of the present invention containing graphical modifiers to the information presented therein. Adjustment indicators 46, in the form of triangles for example, are shown in both an upward and downward orientation. Such a display of adjustment indicators 46 indicates, for example, that at least one medication being taken by a patient interacts with the medication displayed on graphical icon 10 in such a way as to increase the dosage of the medication displayed on graphical icon 10, while at the same time a second medication being taken by a patient interacts with the medication displayed on graphical icon 10 in such a way as to decrease the dosage of the medication displayed on graphical icon 10. Other aspects of the embodiment of the present invention shown in FIG. 3 are described more fully below.

Dosage bar 12 is preferably constructed, in the preferred embodiment of the present invention wherein the present invention is implemented electronically, from a combination of one or more daily doses of a given medication taken by an individual patient. Thus, the length or height of dosage bar 12 preferably represents a total daily dose. It is preferred that dosage bar 12 be provided in one of a number of discrete lengths, rather than in a manner such that dosage bar 12 varies gradually along a continuous dosage gradient, because discrete changes are more readily recognized and interpreted by a user of the present invention. Dosage bar 12 may, for example, be provided in eight possible lengths or heights, each length or height corresponding to a dosage category. Examples of possible dosage categories include, but are not limited to, 'very low dose,' 'low dose,' 'starting dose,' 'moderate dose,' 'moderate/high dose,' 'high dose,' 'very high dose,' and 'extremely high dose.' For the 'very low dose' category, dosage bar 12 may extend only slightly from the bottom of graphical icon 10, while for the 'extremely high dose' category dosage bar 12 may extend along the entire length of one side of graphical icon 10. Other dosage categories are preferably represented by various other heights or lengths between these two extremes. In an embodiment of the present invention wherein a medication icon is used in conjunction with an electronic medical database, a 'starting dose' may be determined automatically by the system, by referring to the database, and the height of dosage bar 12 may be automatically set by comparing the actual dosage a patient is receiving to the 'starting dose' indicated in the medical reference. In other embodiments of the present invention, a user may indicate directly whether the dosage received by a given patient is high, low, moderate, or the like.

Duration bar 14 provides a visual representation of the length of time for which a given patient has been taking the medication represented by graphical icon 10. Duration of medication use is preferably proportional to the length of duration bar 14 up to one year. A duration of use greater than one year is preferably represented by placement of a year indicator 48 (another form of adjustment or augmentation indicator, as described above), in the form of a plus sign for example, for each year as an overlay on duration bar 14 with the length of the bar itself reflective of a partial year of duration. For example, three and a half years of duration would preferably be shown as three year indicators 48 (plus signs in the embodiment shown in the figure) overlaying a bar half the width of the medication icon. When multiple graphical icons 10 are displayed on a screen or elsewhere, a user can determine at a glance the relative time periods over which a patient has been taking each of the various medications prescribed to that patient. In the circumstance in which a patient has not yet begun to take a medication, the area normally occupied by duration bar 14 may be blank, or an empty bar or other graphical indicia may be used as a placeholder to indicate the position of duration bar 14, but that no information is contained therein as yet.

Compliance bar 16 provides a visual representation of a patient's compliance, or lack thereof, with the medication regimen prescribed. A greater height of compliance bar 16 indicates a greater level of compliance on the part of the patient. Other graphical symbols, such as, for example, adjustment indicator 46 shown in FIG. 3, can be used to indicate that while the patient generally complies, the patient sometimes takes more or less than the prescribed dosage. The height or length of compliance bar 16 is preferably proportional to a patient's positive compliance with a prescribed medication dosage. A lower height of compliance bar 16 indicates a low level of compliance in terms of taking the prescribed dosage of a medication (for example, a low height of compliance bar 16 may indicated that a patient is successful in taking a prescribed dosage of medication only 20% of the time). A compliance bar 16 extending along the entire length of one side of graphical icon 10 preferably indicates a patient's 100% compliance in taking the prescribed dosage of a medication. As noted above, information provided by compliance bar 16 (as well as the other bars associated with graphical icon 10) may be augmented by employing various adjustment indicators.

In FIG. 3, for example, adjustment indicators 46 in the form of upward and downward pointing triangles associated with dosage bar 12 indicate that at least two medications are causing a change in dosage for a given patient to whom graphical icon 10 pertains. One such medication is responsible for a decrease in dosage, while the other is responsible for an even greater increase in dosage (it can be seen that the increased dosage outweighs the decreased dosage because three adjustment indicators 46 are present in the upward position, whereas only two point downward). In addition to indicating dosage adjustments based on interactions between two or more medications being taken by a patient, it is contemplated that adjustment indicators may also reflect other patient characteristics such as age, weight, gender, the results of a genetic test, and the like. Also, it is contemplated that rather than using adjustment indicators as described above, the adjusted dosage may simply be reflected by calculating a new height for dosage bar 12 and displaying dosage bar 12 accordingly.

Also in FIG. 3, a plurality of year indicators 48 are present, indicating that the patient has been taking the drug represented by graphical icon 10 for an extended period of time. An adjustment indicator 46 is also associated with compliance bar 16, again in the form of an upward pointing triangle, indicating that while the patient has been complying, the patient has taken it upon herself to take an increased dosage as compared to the amount prescribed by a physician. A downward pointing adjustment indicator associated with compliance bar 16 could be used to indicate that a patient has elected to take less than the prescribed amount of the medication. Finally, a warning indicator 28 is provided along impression bar 18 (described further below) to indicate that the patient has concerns and wishes to discuss them with a physician. Additional warning indicators or adjustment indicators may, of course, be associated with graphical icon 10 as needed.

Impression bar 18 provides a visual representation of a patient's subjective impression of the medication represented by graphical icon 10. The length of impression bar 18 preferably remains constant, with various colors or patterns displayed therein representing a patient's subjective impression of the medication. At a glance, a user is able to determine whether a patient is generally satisfied with a medication, generally dissatisfied with the medication, or in some embodiments of the present invention the specific complaints or feelings the patient has with respect to the medication.

Figure 4:
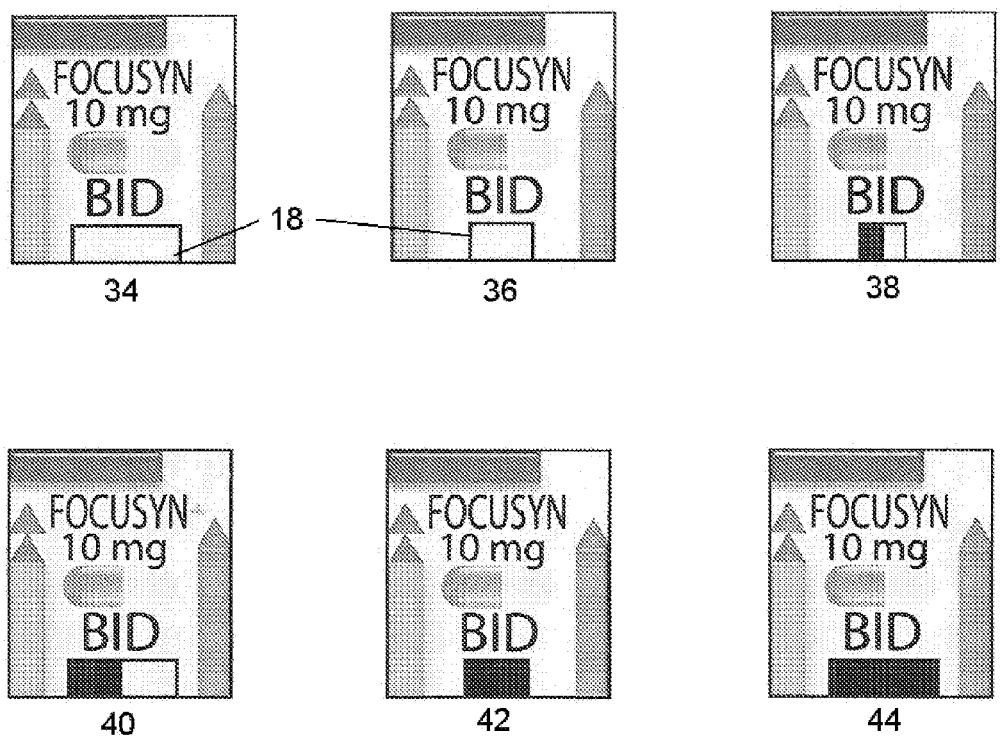
FIG. 4 provides exemplary depictions of various embodiments of a graphical icon of the present invention having differing impression bars associated therewith.

Various exemplary embodiments of impression bar 18 are provided in FIG. 4. Impression bar 18 may be altered, for example, in terms of length and color scheme to reflect any of a number of subjective impressions of a patient taking a medication represented by a graphical icon 10. Thus, at a glance, a physician or other individual can determine a patient's feelings with respect to their use of a given medication. These embodiments of impression bar 18 shown in FIG. 4 are provided with the numerical labels 34 through 44 located underneath the corresponding impression bar 18. With respect to impression bar 18 having the configuration represented by the numeral 34, the lack of coloration and relatively extended length of impression bar indicates that the patient has a 'very favorable' impression of the medication. The configuration of impression bar 18 represented by the numeral 36, wherein the length of impression bar is shorter than that of configuration 34 but wherein the bar still lacks any coloration, indicates that a patient has a 'favorable' impression of the medication. The configuration of impression bar 18 indicated by the numeral 38, wherein the impression bar is relatively short in length and divided in coloration between black and white, indicates a generally neutral impression of the subject medication on the part of the patient. Alternatively, the configuration of impression bar 18 represented by the numeral 40, wherein the bar is divided in coloration between black and white but is longer than that represented by numeral 38, indicates that while a patient is generally satisfied that the medication is effective, there are side effects that concern the patient. Configurations 42 and 44, wherein impression bar 18 is entirely black in color, indicate 'unfavorable' and 'very unfavorable' impressions respectively, based on length of impression bar 18. It should be noted, however, that the above and the depictions of impression bar 18 shown in FIG. 4 are exemplary and not meant to be limiting. Any graphical color, shape, or other suitable scheme may be utilized to represent varying impressions and remain within the scope of the present invention. A user need simply learn the meaning of various configurations, colors, shapes, or other schema in order to, at a glance, assimilate the information being conveyed by impression bar 18.

Preferably centrally located on graphical icon 10 is medication image 20. Medication image 20 is preferably a graphical representation of a single dose of the medication represented on graphical icon 10. It is preferred that medication image 20 reflect the size, shape, color, and other visual characteristics of the actual medication being represented by the icon. Thus, graphical icon 10, in addition to the other functions described above, serves as a visual means of reducing confusion between various medications by a user or patient taking more than one medication.

Text box 22 is preferably provided for inclusion of any desired textual information within graphical icon 10. Such information may include, but is not limited to, the name of a medication with which graphical icon 10 is associated, a typical dosage of the medication, a frequency of dosing, or any other desired information. Additional text boxes may be placed at various locations within graphical icon 10 in order to convey additional textual information as desired.

In some embodiments of the present invention, graphical icon 10 preferably further includes other useful information with respect to the medication being represented. Such information includes, but is not limited to, the amount of medication contained within each pill, capsule, or tablet (e.g. 100 mg, 500 mg, and the like), the number of pills that should be taken in order for a patient to receive a single dose, and the frequency at which a patient should be taking the medication (e.g. once per day, twice per day, and the like). A medical reference database associated with the present invention preferably includes information correlating the height of dosage bar 12 with a numerical dosage and a text descriptor. For example, a given height of dosage bar 12 for the drug Seroquel may indicate a dosage of from 50 to 150 mg per day, and an associated text descriptor of "low." In a situation where a patient takes, for example, 25 mg of Seroquel three times per day, the present system sums the total daily dosage to 75 mg and then extends the height of dosage bar 12 to that corresponding to a low dosage. It is contemplated that any other desired information may be represented graphically or otherwise on graphical icon 10, thereby providing that information to a user of the present invention, or a patient, at a glance.

In addition to the above, in one aspect of the present invention, a user of the present system can click and drag the various bars of a graphical icon 10 to reflect changes in patient dosing, disposition, and the like. For example, a user can click and drag compliance bar 16 from the one-hundred percent position to the ten percent position in a situation where a patient initially indicated that his compliance with a prescribed medication regimen was one-hundred percent during a given time period, and then later admits during a session with the health care provider that the true compliance figure is ten percent. In a preferred embodiment of the present invention, wherein the medication icon embodiment of the invention is associated with an electronic medical record or patient database, dragging or otherwise manipulating the various bars of the medication icon results in a corresponding change in the patient's file in the medical record or other database.

In another aspect of the present invention, a user may use keyboard or mouse maneuvers, or voice commands, to change future medication instructions. For example, the user may drag dosage bar 12 from a low level to a moderate level. This aspect of the present invention is preferably associated with an electronic medical record or patient management system with which the present graphical icons 10 are being used. In some instances, such a change may also be reflected in an electronically-generated prescription.

It is preferred that in electronic embodiments of the present invention, a user can acquire additional information relating to any information displayed on graphical icon 10 by, for example, placing a mouse cursor over any information displayed on a graphical icon 10 (a maneuver known as a 'mouseover'). When a mouseover is performed, for example, on an adjustment indicator 46, a small popup box may appear providing details as to which medications are interacting with the medication displayed on graphical icon 10, thereby causing an adjustment in the dosage indicated on graphical icon 10. Likewise, performing a mouseover of dosage bar 12, duration bar 14, compliance bar 16, or impression bar 18 may result in a popup box providing addition information, such as standard or normal dosages of a given medication, the actual amount of time over which a patient has been taking a medication, a patient's precise compliance rate with a displayed medication, comments by a patient or physician concerning a patient's impression with a displayed medication, or any other desired information. A user may also perform a mouseover of medication image 20 or text box 22 (or any other portion of a graphical icon 10) to acquire additional information relating that displayed on graphical icon 10.

In addition to the above, it is contemplated that in some cases a combined medication icon 100 may be used in place of graphical icon 10. Combined medication icon 100 is preferably used for common medication combinations for which it makes clinical sense to incorporate the information provided for both medications into a single icon. An exemplary embodiment of combined medication icon 100 is provided in FIG. 5.

Figure 5:
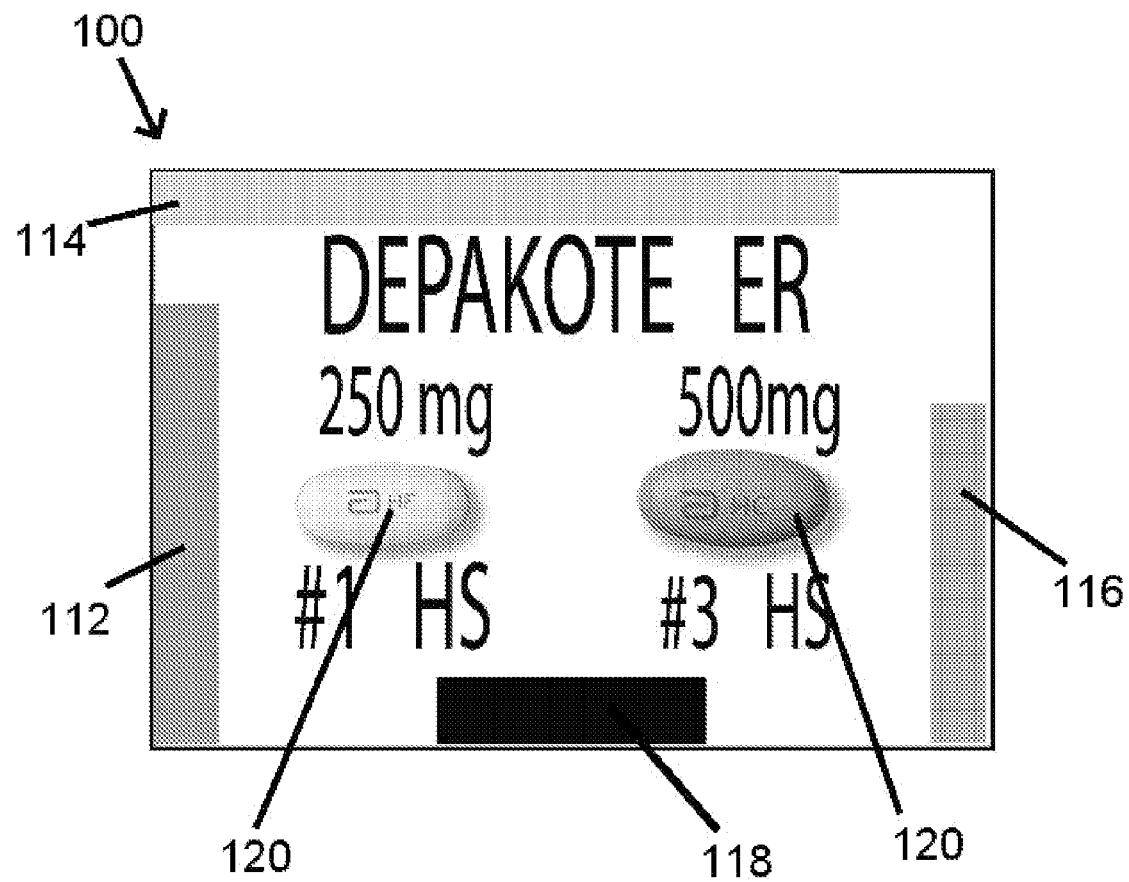
FIG. 5 is a diagram of an exemplary embodiment of a combined medication icon of the present invention.

As shown in FIG. 5, combined medication icon 100 preferably includes a dosage bar 112 indicating the combined dosage of the two medications represented by combined medication icon 100. In the example shown, dosage bar 112 indicates a dosage level of 1750 milligrams, corresponding to 1×250 milligrams of Depakote and 3×500 milligrams of ER. The other aspects of combined medication icon 100 function generally as described with respect to graphical icon 10, above, including duration bar 114, compliance bar 116, impression bar 118, medication image 120, text box 122, and the like. The height of dosage bar 112 is preferably automatically set based on a summation of the daily doses taken, as with dosage bar 12 described above. Further, any of the adjustment indicators or other augmentations or variations described above with respect to graphical icon 10 may be utilized with respect to combined medication icon 100 as well.

Figures 6, 7:
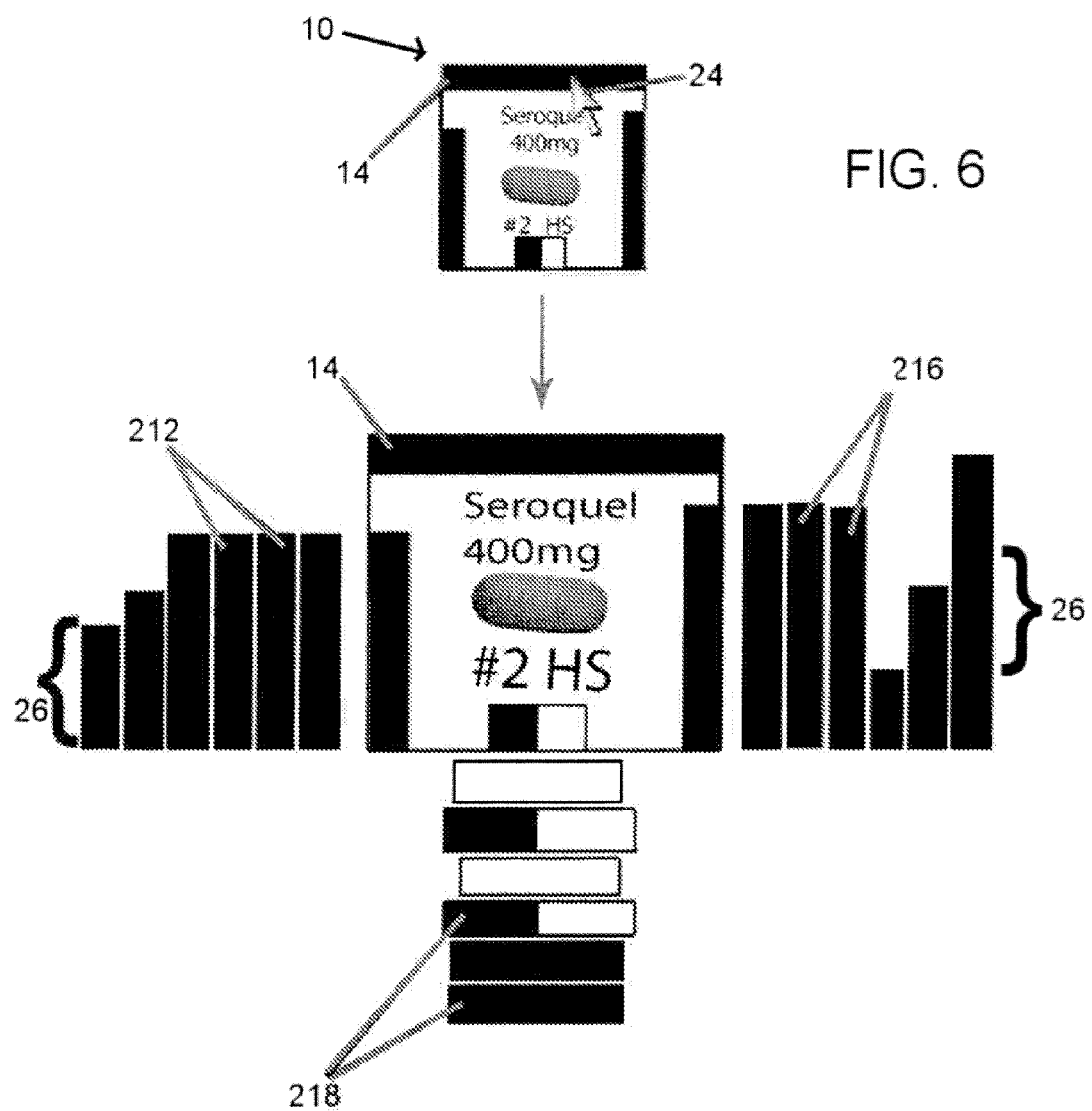
FIG. 6 is an exemplary embodiment of a graphical icon of the present invention having a cursor positioned over a duration bar thereof.
FIG. 7 is a diagram of an exemplary embodiment of a graphical icon of the present invention having past medication bars shown associated therewith.
Figure 8:
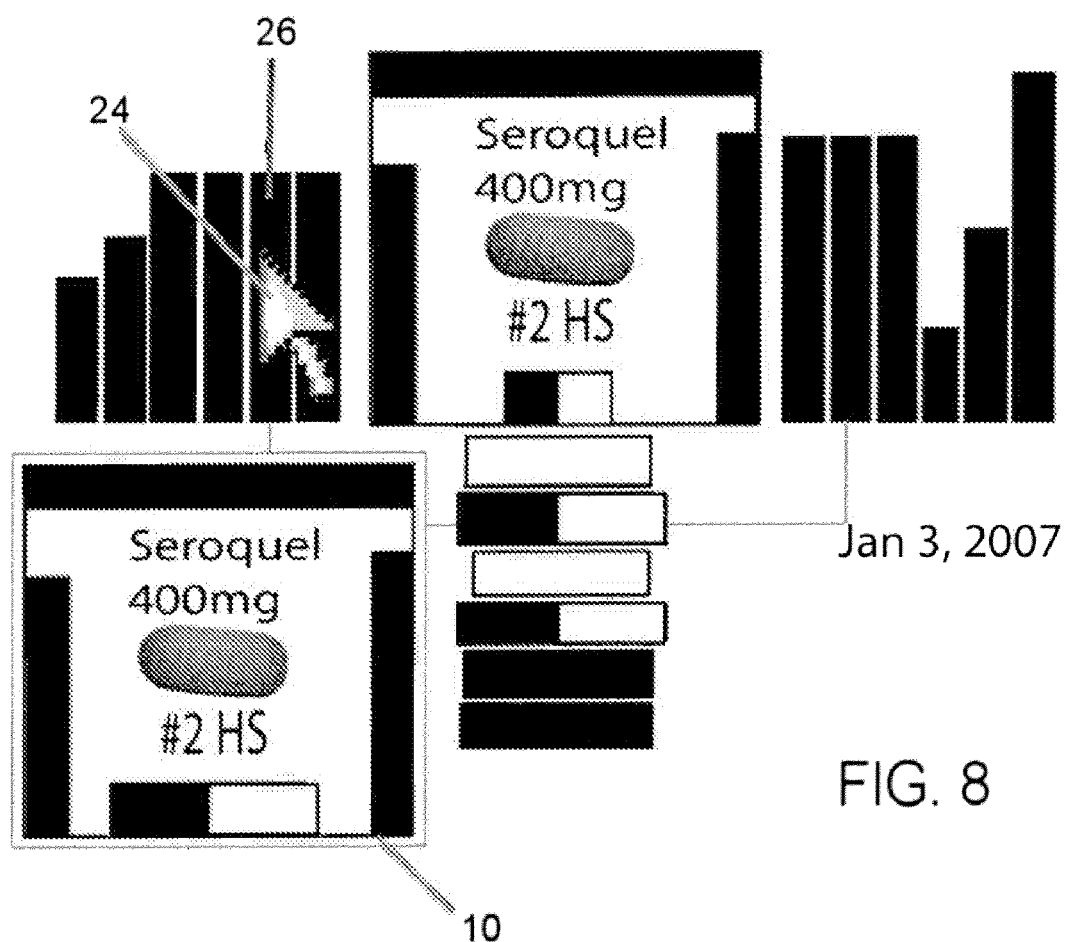
FIG. 8 is a diagram of an exemplary embodiment of a graphical icon of the present invention having past medication bars shown associated therewith and further having a past graphical icon shown associated therewith.

FIGS. 6 through 8 illustrate another aspect of the graphical icons 10 of the present invention, which is the ability to quickly review historical information, such as the past medication history of a given patient via the graphical icons 10 of the present invention. FIG. 6, for example, illustrates a typical graphical icon 10 of the present invention, with a cursor 24 positioned over a duration bar 14 thereof. In this embodiment of the medication icons of the present invention, clicking on duration bar 14, without performing a dragging motion to resize the bar, results in the display of past medication bars 26 in a histogram-like arrangement alongside graphical icon 10, as shown in FIG. 7. Past or discontinued medication bars 26 are preferably provided in grayscale, whereas the various bars associated with current medications represented by graphical icon 10 are provided in color.

Past medications bars 26 are shown in FIG. 7 associated with a graphical icon 10. Past medication bars 26 include past dosage bars 212, past duration bars 214, past compliance bars 216, and past impression bars 218. These bars provide, at a glance, a significant amount of information concerning the medication history of a given patient. Thus, past dosage bars 212 may provide a user with a history of the dosage of the represented medication received by a given patient, or may provide dosage information for other medications that were prescribed to that patient in the past. Past compliance bars 216 may provide a history of a patient's compliance with the medication represented by graphical icon 10, or may provide a general history of a patient's compliance with any or all other medications prescribed to that patient, either currently or in the past. Past impression bars 218 may provide a history of a patient's subjective impression of the represented medication over time, or may provide generally a history of a patient's impression of all medications prescribed, at present or in the past, such that a user can identify whether a patient is predisposed to have a positive, negative, or neutral impression of a prescribed medication. In some embodiments of the present invention, past medication bars 26 may also be associated with a textual representation of the date upon which the past medication was prescribed and/or changed. Further information regarding each of past medication bars 26 may be retrieved by placing cursor 24 over past medication bars 26, as shown in FIG. 8, thereby causing the display of a complete graphical icon 10 associated with the past medication bar 26 over which cursor 24 is positioned.

Figure 9:
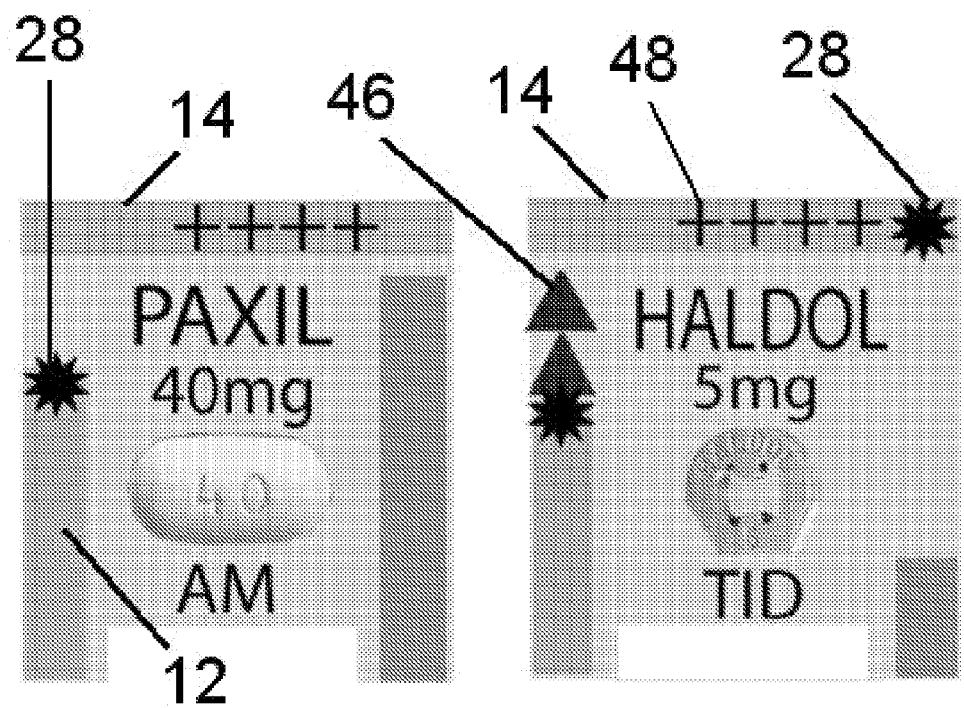
FIG. 9 is a diagram of two exemplary embodiments of graphical icons of the present invention having various indicators associated therewith.

FIG. 9 provides further exemplary features of one embodiment of the present invention, these features being associated with the exemplary medication icon embodiment of graphical icon 10. In the figure, for example, dosage bar 12 of the graphical icon 10 displaying information for the drug Paxil® includes a warning indicator 28 in the form of a black star (any suitable graphical or textual representation may be used for a warning indicator 28). A warning indicator 28 in dosage bar 12 of a graphical icon 10 preferably indicates an interaction or contraindication relating to, for example, another medication being taken by a patient, or a diagnosis or physical condition of the patient. Warning indicator 28 serves to indicate to a user that there is an important interaction or contraindication associated with the use of the drug represented by graphical icon 10, but that this interaction or contraindication does not result in an altered dosage of the drug. A user may preferably mouseover the warning indicator to receive more information about the warning in the form of a popup box. In a circumstance wherein a change of dosage is necessitated due to an interaction or other indication, an adjustment indicator 46, such as in the form of a triangle, may be displayed above dosage bar 12, such as that shown in FIG. 9 as associated with the graphical icon 10 for Haldol®. In the situation depicted in FIG. 9, the fact that a patient is taking Paxil® results in an increased dosage of Haldol®, as indicated by the two adjustment indicators 46 in the form of upwardly-pointing triangles. In a situation wherein a decreased drug dosage is required due to a drug interaction or other indication, adjustment indicator 46 preferably takes the form of a downward-pointing triangle located on dosage bar 12. Although the triangular form of adjustment indicator 46 is preferred, any suitable graphical or textual representation may be used.

Graphical icons 10 in FIG. 9 further include year indicators 48, provided in the form of 'plus' signs or crosses associated with duration bar 14. In a preferred embodiment of the invention, year indicators 48 indicate a duration of one year during which a patient was taking the medication represented by the icon. Each subsequent appearance of a year indicator 48 on a graphical icon 10 indicates an additional year of duration. As can be seen in the figure, a warning indicator 28 may also be present associated with duration bar 14. Such a warning indicator located on dosage bar 12 may indicate to a user that an important situation exists with respect to the medication represented by graphical icon 10 and the patient at issue. For example, warning indicator 28 associated with duration bar 14 may indicated that a patient has been taking a medication for too long, and that the time has come for a change in the patient's dosage. Likewise, in situations where one medication prescribed to a patient is being replaced by another, such as for example by cross-titration, warning indicator 28 may indicate that it is time to further reduce the dose according to the cross-titration scheme, or that the medication at issue may now be eliminated entirely.

Also with respect to FIG. 9, it can be seen that the medication images associated with the graphical icons in the figure are distinctive and give a realistic impression of the actual appearance of the medication. Thus, graphical icon 10 aids in preventing confusion and mistake with respect to two or more medications.

As noted above, with respect to any of the various embodiments of graphical icon 10 described herein, it is preferred that a text box be provided onscreen (in the form of a popup, for example) when a mouse cursor is placed over a given portion of the medication icon. For example, when a mouse cursor is placed over impression bar 18, a text box pops up preferably providing additional information about a patient's impression of a medication. Likewise, a mouse cursor placed over the dosage, duration, or compliance bars preferably provides further information concerning those aspects of the patient at issue. Placing a cursor over the image of the medication or, alternatively, the name of the medication, may provide a pop-up box containing various available dosages, or out-of-pocket cost for that medication on the part of a given patient (taking into account health insurance co-pay, lack of insurance, and the like). Further, placing a mouse cursor over a specific portion of graphical icon 10 pertaining to, for example, dosage, dose schedules, and the like, preferably allow a user to change those variables from that computer screen, without having to navigate elsewhere into the program. It is preferred that a user may even change the prescribed medication by clicking on a graphical icon 10 itself.

In addition to the various features of the present invention described above, it is further contemplated that the appearance or other features of a graphical icon 10 of the present invention may be customized by a user thereof. This customization may occur by allowing a user to selection certain optional components (such as, for example 'plugins') to be associated with graphical icons 10 displayed to that user. Such plugins or optional components may be provided with a software package that includes graphical icons 10 according to the present invention, or may be available for download or order apart from the original software package obtained by a user.

One example of such customization of features of graphical icon 10 is simply a change of coloration of one or more elements of graphical icon 10 (such as a dosage or other bar, warning indicator, and the like). Under specified conditions a user may wish a bar or other indicator to change color in order to more readily alert the user to the information represented by the bar or other indicator. For example, a user may wish to have compliance bar 16 represented in red if a patient's compliance drops below a predetermined level. Compliance bar 16 could be represented in yellow to indicate that noncompliance is nearing the predetermined threshold, and the color green could be used to indicate an acceptable level of compliance. The color of any or all of the elements of a graphical icon 10 may be customized by a user in embodiments of the present invention having that functionality.

In addition to, or in lieu of, color changes, a user of graphical icons 10 may also employ any of numerous other customizations or modifications, according to the user's desire or need, in order to draw attention to data represented by graphical icon 10. For example, a flag in the form of a graphical or textual element may be positioned over an element of graphical icon 10 (such as a bar, indicator, or other element) to indicate to a user that the value represented by that element has fallen within a predetermined range, or simply that the value has changed. Likewise, rather than placing a flag over the element to which a user's attention is to be drawn, the element may be represented in a pulsating or blinking form, or with a halo displayed around the element. Graphical icons 10 as a whole may be distorted in shape or may be represented as bouncing boxes when data displayed thereon has changed or falls within a predetermined ranged deemed by a user to be of importance.

The examples detailed above represent only a few of many possible customizations that may be made by an end user to render the graphical icons of the present invention even more useful in terms of conveying information. Such modifications and customizations may be made available to a user by providing add-ons or plugins to software incorporating graphical icons 10, or may be provided as options selectable within the off-the-shelf software application, without the need for the addition of functionality to the software. Many other customizations will be readily apparent to those of skill in the art upon reading this disclosure, and it is contemplated that these other customizations fall within the spirit and scope of the present invention.

In addition to user-defined customization of a graphical icon 10 of the present invention, it is further contemplated that a graphical icon 10 of the present invention may be provided in three-dimensional shape, such as in the shape of a cube. In such a six-sided three-dimensional embodiment, for example, each face of the cube may provide additional information described above in a two-dimensional format. A user may rotate the three-dimensional graphical icon 10 by, for example, manipulating the icon with a mouse. In a preferred embodiment of a three-dimensional graphical icon, rotating the three-dimensional cube-like icon reveals another face of the three-dimensional object, this face having, for example, historical data associated therewith. In the example of graphical icon 10 shown in FIG. 7, for example, the historical data, such as past dosage bars 212, may be wrapped around the three-dimensional object such that the data is present on a different face of the cube from the graphical icon proper, which is originally oriented toward a user of the present invention. Thus, rotating the cube to the right, and therefore exposing a left side of the cube from the point of view of a user, may expose past duration bars 212, while rotating the three-dimensional icon to the left may expose past compliance bars along a right side of the cube. Rotating the three-dimensional icon in an upward direction may expose the underside of the cube, which contains, for example, past impression bars 218. It is contemplated that any suitable three-dimensional shape may be employed and that any desired information may be provided on the surfaces of the three-dimensional object other than that depicting the graphical icon proper.

With respect to the medication icon embodiment of the present invention described above, it is contemplated that a set of medication icons, when used in conjunction with an electronic medical record, patient management software, patient database, or other patient management system, represents a given patient's medication list, with each medication icon displayed representing, preferably, a single medication on the patient's medication list. Thus, a medication icon set provides a user, at a glance, the list of medications being taken by a given patient, and all of the data described above concerning any individual medication being taken.

Although the above-described exemplary embodiments of the present invention are directed primarily to the health care professions, and more specifically to the mental health professions, it is contemplated that the principles of the present invention may be adapted to a number of varied occupations, professions, trades, or art areas. The application of the present invention to other occupations, professions, trades, or art areas will be described in more detail below.

An underlying principle of the present invention is the presentation of data in a novel format that is easy to understand and readily conveys the desired information to an audience. The present invention is discussed now, in more general form, with a discussion following of exemplary ways in which the invention may be applied to various uses, professions, fields of endeavor, art areas, and the like, based upon the general principles disclosed herein.

Figure 10:
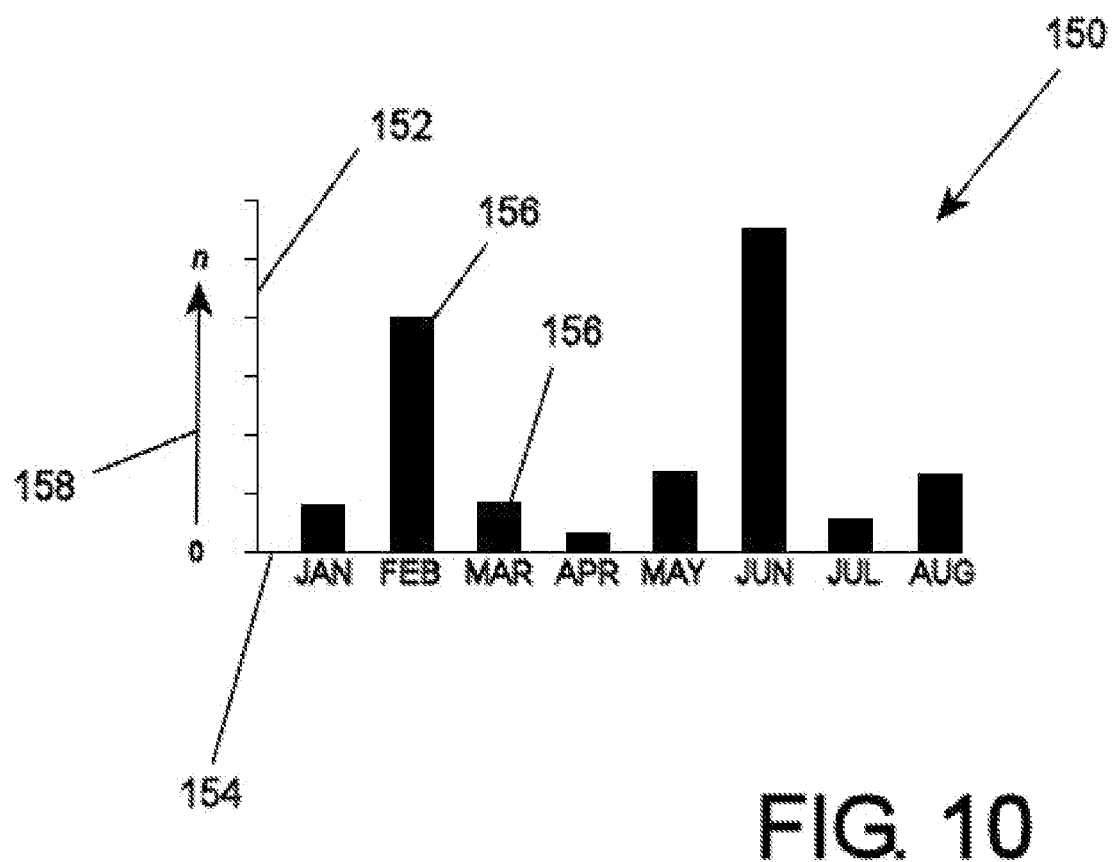
FIG. 10 provides an illustration of a typical bar graph of the type known in the art.

FIG. 10 depicts a bar chart or bar graph 150 of the sort commonly used in the presentation of data. Bar graph 150 includes a first axis 152, which extends along a range of numerical values from, as indicated in this exemplary illustration by arrow 158, zero to n. A second axis 154 is also provided, although second axis 154 typically has no value in and of itself, numerical or otherwise, serving primarily to anchor the bottom of bar graph 150 and provide a space upon which bars 156 are presented. Second axis 154 is sometimes referred to as a 'data grouping axis' because the data begin displayed on the bar graph is grouped along that axis.

Bars 156 of bar graph 150 extend from second axis 154 upward to a point equivalent to a desired height along first axis 152, namely the point at which the height of bar 156 corresponds to a desired numerical value along first axis 152. Each bar 156 is typically labeled with an indicator relating to a user of bar graph 150 the data or values being represented by bars 156. For example, bar graph 150 may provide a user with the total rainfall in a given area on a monthly basis. The rainfall may be represented, in inches, as a value between zero and n along first axis 152, with bars 156 representing, from left to right, the months of January, February, March, April, and so on. It is contemplated that bar graphs such as bar graph 156 are well known and the above serves only as a brief, exemplary description of such graphs.

While bar graphs are well known and are quite useful in terms of conveying information, the present invention relies on a more compact, iconic representation of information that conveys more information than a typical bar graph using the same amount of space, and conveys the information in a more engaging manner.

Figure 11:
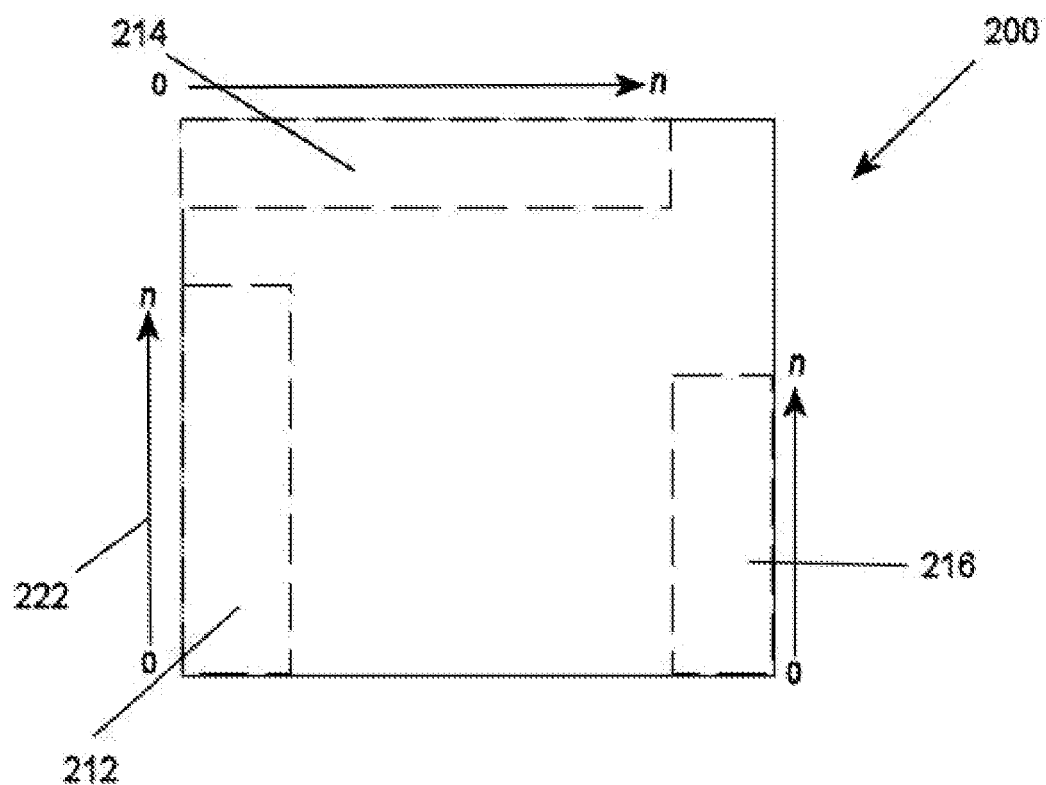
FIG. 11 provides a schematic illustration of one embodiment of a graphical icon of the present invention, the icon not being associated with any particular data or data type.

FIG. 11 provides a schematic diagram illustrating some of the various principles underlying the present invention. The figure provides a graphical icon 200 having sections outlined along three axes for inclusion of data therealong. Arrows 222 indicates the direction of the various axes, which in the exemplary drawing shown in FIG. 11 extend from zero to n. It is contemplated, however, that any of the various axes shown in FIG. 11, or utilized with respect to any other embodiments of the present invention, may have any useful value, including but not limited to any numerical range.

A first data area 212 is shown along a left-most axis of graphical icon 200, extending from a bottom-most portion of graphical icon 200 in an upward direction. Data area 212 is provided in the form of a dashed line indicating, for example, where a bar such as those described above with respect to the medication icon embodiment of the present invention may be positioned (duration bar 12, for example). It is contemplated, however, that data area 212 may take any suitable form, including but not limited to that of a bar or other geometric shape. A second data area 214 is shown along an upper-most axis of graphical icon 200, extending from a left-most edge of graphical icon 200 and to the right. Once again an arrow is provided showing the direction of this axis of graphical icon 200 extending across a range from zero to n. As with the axis indicated by arrow 222, the axis extending across the top-most portion of graphical icon 200 is not limited to numerical values but may include any useful values. Further, in the instance where a numerical range is provided, any numerical range may be used and the left-most portion of the axis need not represent zero. A third data area 216 is also provided, this data area extending along a right-most axis of graphical icon 200, extending from a bottom-most portion of graphical icon 20 in an upward direction. An arrow is also provided indicating the direction of the right-most axis of graphical icon 200, but it is once again contemplated that this representation of the axis is exemplary only, and does not limit the present invention. As with data area 212, data areas 214 and 216 take the form of a dashed line showing a potential placement of a bar such as the various bars described above with respect to the medication icon embodiment of the present invention. It is contemplated, however, that data areas 214 and 216, like data area 212, may take any suitable form, including but not limited to that of a bar or other geometric shape.

Figure 12:
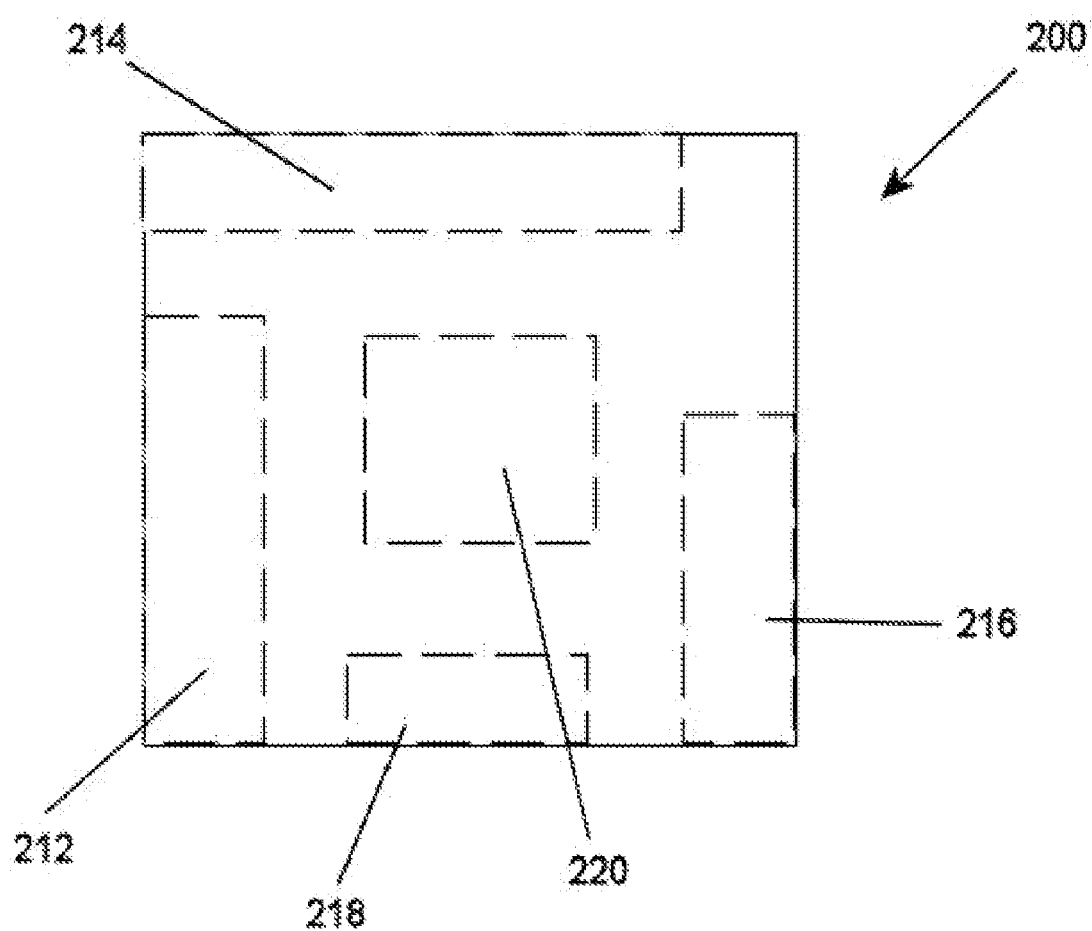
FIG. 12 provides a schematic illustration of another exemplary embodiment of a graphical icon of the present invention, the icon not being associated with any particular data or data type.

FIG. 12 provides a schematic illustration of a graphical icon 200 such at that shown in FIG. 11, with additional features added thereto. Although not shown in FIG. 12, it is contemplated that the various axes of graphical icon 200 are substantially the same as those depicted in FIG. 11 and described above. The embodiment of graphical icon 200 shown in FIG. 12 further includes a fourth data area 218, which is provided in the form of a dashed line outlining a bar along the bottom center of graphical icon 200. Any suitable form of data area 218 may be utilized, whether in the form of a bar or other geometric shape. Also shown in FIG. 12 is content area 220, which may contain text, images, designs, logos, or any other suitable content desired to be provided along with graphical icon 200.

Figure 13:
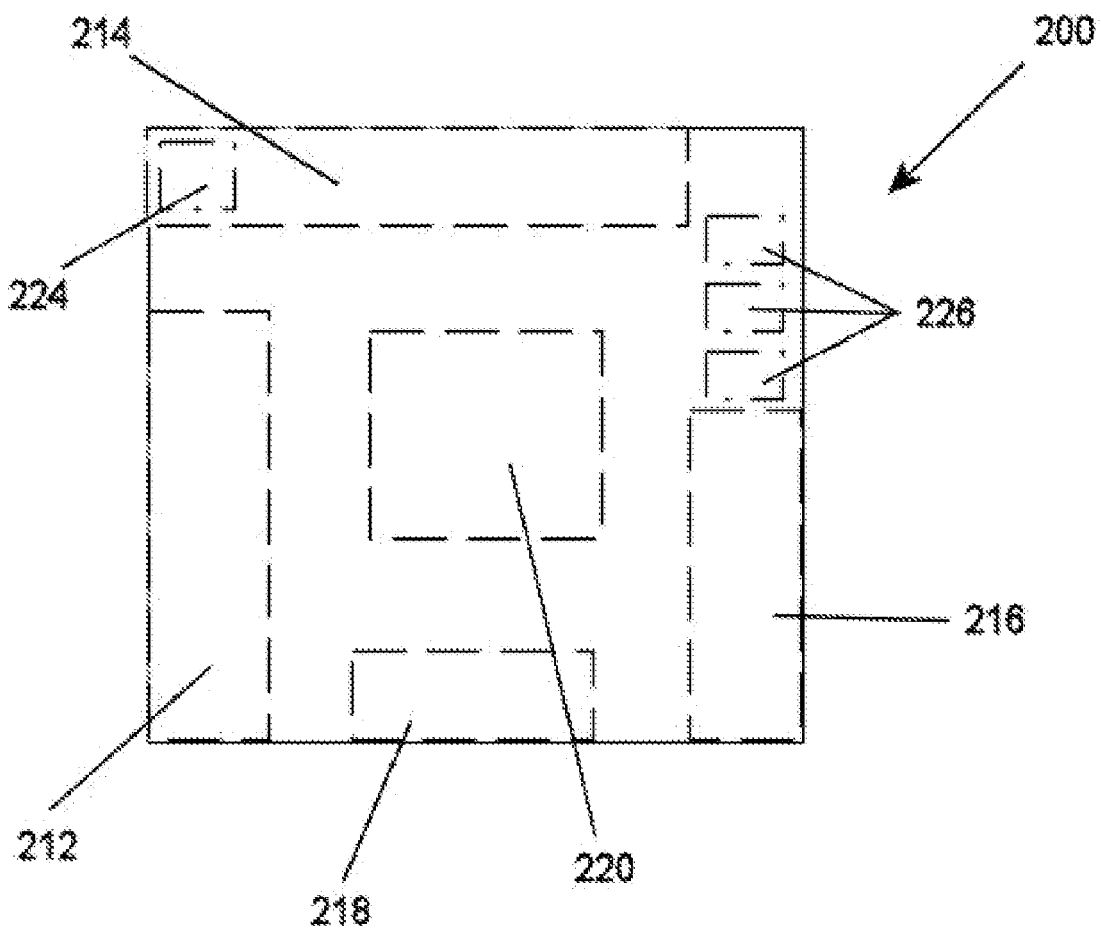
FIG. 13 provides a schematic illustration of another exemplary embodiment of a graphical icon of the present invention having data augmentation areas included thereon, the icon not being associated with any particular data or data type.

FIG. 13 provides a schematic illustration of another embodiment of graphical icon 200, this embodiment adding to the features of graphical icon 200 shown in FIG. 12. Specifically, data augmentation areas 224 and 226 are shown in exemplary positions. Any suitable content may be used in these areas to augment the data already being provided by a graphical icon 200. For example, images, text, numbers, mathematical symbols, and the like may be used. Any suitable number of data augmentation areas may be provided with graphical icon 200, and these may be located directly on top of any of the various data indicators 212, 214, 216, or 218, along any edge thereof, or either before the beginning of a data indicator or after the end thereof. Examples of images or symbols that may be used in data augmentation areas 224 and 226 include, but are not limited to, adjustment indicators 46, year indicators 48, and warning indicators 28 described with respect to the medication icon embodiment of a graphical icon 10 of the present invention.

Figure 14:
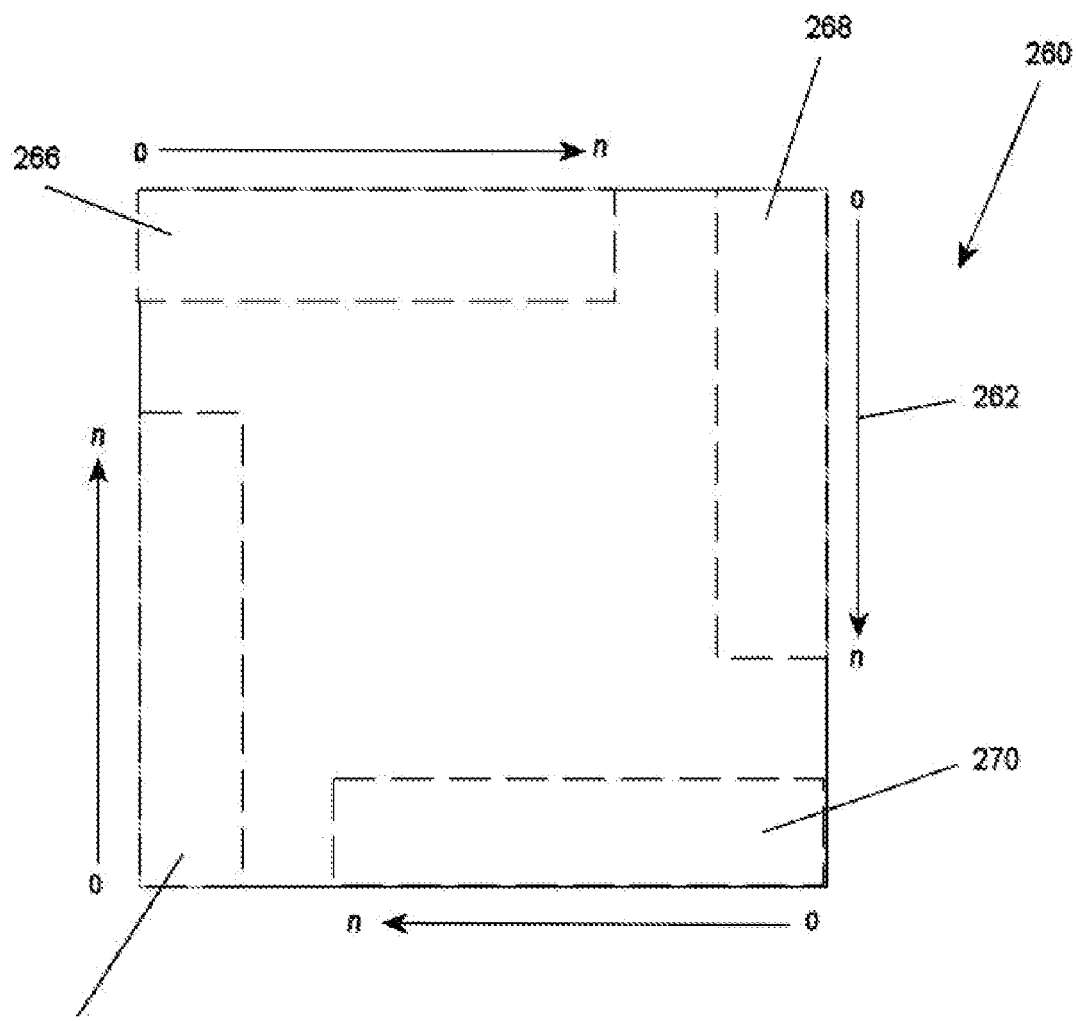
FIG. 14 provides a schematic illustration of another exemplary embodiment of a graphical icon of the present invention, the icon not being associated with any particular data or data type.

FIG. 14 provides a schematic illustration of an alternative embodiment of a graphical icon 260. This figure is exemplary and is employed to depict one possible alternative arrangement of axes and data areas in association with a graphical icon 260 of the present invention. Graphical icon 260 includes an axis extending from zero to n at each of the four corners of the icon. Data areas 264, 266, 268, and 270 are provided, each extending along an edge of graphical icon 260 corresponding with an individual axis. As with the other embodiments of a graphical icon described above, the various data areas shown in FIG. 14 may contain any suitable data indicator, such as a bar or other geometric shape. Likewise, as with the embodiments of the present invention described above, the axes shown in FIG. 14 may extend along any numerical range, or may be directed to non-numerical values or any combination of numerical and non-numerical values.

It is contemplated that the various depictions and descriptions of graphical icons 200 and 260 do not limit the present invention to the structure or layout of the graphical icons shown or described. Data indicators, content areas, data augmentation areas, and other portions of the graphical icons of the present invention may be arranged in any suitable manner, with any suitable axes being present, or with any of the various axes being eliminated as needed or desired. Likewise, the direction of the various axes may be altered in any suitable manner. The graphical icons of the present invention may include any geometric shape, with a bar graph or other data-conveying visual element encapsulated within the geometric shape, and the walls of the geometric shape serving as axis upon which the data is plotted or otherwise displayed. Data indicators may be of various sizes, shapes, and colors, with any or all of the attributes being tied directly to the information being imparted by the data indicator. The principle underlying the present invention rests in the presentation of a large amount of complex data in a compact, readily-understandable iconic form. It is contemplated that numerous variations on this principle will be readily apparent to those of skill in the art upon reading this disclosure, and that those variations are captured by the present invention.

As noted above, the principles of the present invention may be applied to numerous professions, trades, art areas, occupations, and the like, and some of these possible applications are now briefly described. The principles of the present invention, for example, could be applied in the legal field, wherein a graphical icon contains information relating to the legal history of a client, the types of issues with which a client typically needs assistance, or even currently-pending issues, important dates, billing information (including status of past invoices), and the like. Expanding an icon to show historical data, as shown, for example, in FIG. 7 above, could provide a great deal of additional information about the history of a pending case or action.

The principles of the present invention could also be applied to the automotive repair industry, with the history graph features of the present invention being adapted to show the entire history of a given automobile, including accidents, prior repairs, recalls, and the like. General information contained within a given icon could provide a mechanic or other professional with pertinent information applying to a specific make and model of vehicle, whereas customer-specific information could provide information relating to the customer's maintenance habits, payment history, and the like.

With respect once more to medications, graphical icons of the present invention may be used by an entity during a drug development and approval process to provide a quick informational source relaying to a scientist or business executives the characteristics of a newly-developed drug, dosage information, safety information, and the length of time the drug has been in the approval process, the current status of approval, status of intellectual property protection, and important upcoming dates in the drug development and approval process.

In addition, the principles of the present invention may be associated with graphical icons representing files, folders, applications, and the like on a computer desktop, with various indicators providing information concerning, for example, frequency of use information, user permissions, creation information, and the like, relating to the various files, folders, and applications. In the case of applications that require periodic updates, indicators associated with a graphical icon of the present invention and displayed on the computer desktop may also provide information concerning the existence of an update, the priority level of the update, and the like.

The preferred embodiments of the present invention are displayed electronically, such as on a computer screen, and may be referred to herein as electronic graphical icons. Non-electronic embodiments of the present graphical icons such as those described herein could be provided, for example, on a paper insert provided with a medication, providing a physician or user with an at-a-glance accumulation of information pertaining to that specific drug, including dosage information, indications and contraindications, and the like.

The principles of the present invention may be successfully applied to any situation in which a volume of complex and/or historical information is required to be displayed to a user in a manner that renders the information quickly understandable and assimilated.

It is contemplated that upon reading this disclosure one of skill in the art could reasonably adapt the principles of the present invention to any of these or various other art areas, and such uses of the principles of the present invention are considered to be within the spirit and scope of the present invention.

The detailed description set forth above is provided to aid those skilled in the art in practicing the present invention. The invention described and claimed herein, however, is not to be limited in scope by the specific embodiments disclosed because these embodiments are intended to be illustrative of several aspects of the invention. Any equivalent embodiments are intended to be within the scope of the present invention. Various modifications of the invention that do not depart from the spirit or scope of the present invention, in addition to those shown and described herein, will become apparent to those skilled in the art from the foregoing description. Such modifications are also intended to fall within the scope of the appended claims.

The invention claimed is:

1. computer-implemented method of providing information regarding a patient's use of medications, the method comprising the steps of:
   a) accessing a database having information relating to a medication being taken by a patient; and
   b) generating a dosage indicator from information in said database pertaining to a dose of said medication being taken by the patient;

c) generating a duration indicator from information in said database pertaining to a duration of said patient's use of medication;

d) generating a compliance indicator form information in said database pertaining to said patient's compliance with a prescription of said medication;

e) generating a historical impression indicator from information in said database pertaining to said patient's subjective impression of said medication;

f) generating a graphical icon, said icon incorporating in graphical form at least a portion of the information relating to a medication being taken by a patient, the graphical icon comprising a closed geometric shape having a first edge defining a first discrete axis of data and having said dosage indicator extending therealong, a second edge defining a second discrete axis of data and having said duration indicator extending therealong, a third edge defining a third discrete axis of data and having said compliance indicator extending therealong, and a fourth edge defining a fourth discrete axis of data and having said historical impression indicator extending therealong, the historical impression indicator representing, graphically, said patient's subjective impression of the medication over time; and g) displaying said graphical icon to a user;

wherein steps a) through g), above, are performed by a computer programmed to perform said steps.

2. The method according to claim 1 wherein at least one of said indicators provides historical information regarding said patient's use of said medication.

3. The method according to claim 1 wherein said graphical icon further includes an image of said medication.

4. The method according to claim 1 further comprising the step of:

h) repeating steps a) through g), above, with respect to each medication being taken by said patient, thereby providing a set of graphical icons representing the entirety of the medications being taken by said patient.

5. A non-transitory computer readable medium storing instructions hereon that when executed by a processor cause the processor to:

a) accessing a database having information relating to a medication being taken by a patient; and b) generating a dosage indicator from information in said database pertaining to a dose of said medication being taken by the patient;

c) generating a duration indicator from information in said database pertaining to a duration of said patient's use of the medication;

d) generating a compliance indicator form information in said database pertaining to said patient's compliance with a prescription of said medication;

e) generating a historical impression indicator from information in said database pertaining to said patient's subjective impression of said medication;

f) generating a graphical icon, said icon incorporating in graphical form at least a portion of the information relating to a medication being taken by a patient, the graphical icon comprising a closed geometric shape having a first edge defining a first discrete axis of data and having said dosage indicator extending therealong, a second edge defining a second discrete axis of data and having said duration indicator extending therealong, a third edge defining a third discrete axis of data and having said compliance indicator extending therealong, and a fourth edge defining a fourth discrete axis of data and having said historical impression indicator extending therealong, the historical impression indicator representing, graphically, said patient's subjective impression of the medication over time; and g) displaying said graphical icon to a user;

wherein steps a) through g), above, are performed by a computer programmed to perform said steps.

6. The computer readable medium according to claim 5 wherein the graphical icon comprise image of said medication.

7. The computer readable medium of claim 5 further comprising an adjustment indicator associated with at least one of said dosage, duration, compliance, and historical impression indicators.

8. The computer readable medium of claim 5 further comprising a warning indicator associated with at least one of said dosage, duration, compliance, and historical impression indicators.

9. The graphical icon of claim 5 further comprising a year indicator associated with said duration indicator.

10. The computer readable medium of claim 5 further comprising a text portion for conveying textual information to a user thereof.

11. The computer readable medium of claim 5 further comprising an image portion for displaying an image relating to said subject matter of said graphical icon.

* * * * *